United States Patent
Wilson

(10) Patent No.: US 9,463,319 B2
(45) Date of Patent: Oct. 11, 2016

(54) LOW PULSE RATE COCHLEAR IMPLANT STIMULATION IN CONJUNCTION WITH A SEPARATE REPRESENTATION OF FUNDAMENTAL FREQUENCIES AND VOICED/UNVOICED DISTINCTIONS

(75) Inventor: Blake S. Wilson, Durham, NC (US)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1453 days.

(21) Appl. No.: 12/879,159

(22) Filed: Sep. 10, 2010

(65) Prior Publication Data
US 2011/0066210 A1 Mar. 17, 2011

Related U.S. Application Data

(60) Provisional application No. 61/241,438, filed on Sep. 11, 2009.

(51) Int. Cl.
*A61N 1/36* (2006.01)
*A61F 11/04* (2006.01)
*A61N 1/05* (2006.01)

(52) U.S. Cl.
CPC .......... *A61N 1/36032* (2013.01); *A61F 11/045* (2013.01); *A61N 1/05* (2013.01); *A61N 1/056* (2013.01); *A61N 1/0541* (2013.01)

(58) Field of Classification Search
USPC ............................................. 607/48, 57, 25
See application file for complete search history.

(56) References Cited

U.S. PATENT DOCUMENTS

| 4,532,930 A * | 8/1985 | Crosby et al. ................. 607/57 |
|---|---|---|
| 6,231,604 B1 | 5/2001 | von Ilberg ..................... 623/10 |
| 7,421,298 B2 * | 9/2008 | Daly et al. ..................... 607/57 |
| 2001/0031996 A1 * | 10/2001 | Leysieffer ...................... 607/57 |
| 2004/0082980 A1 * | 4/2004 | Mouine et al. ................. 607/48 |
| 2008/0039771 A1 | 2/2008 | Jolly .............................. 604/20 |
| 2008/0064918 A1 | 3/2008 | Jolly .............................. 600/25 |
| 2009/0018616 A1 | 1/2009 | Quick et al. .................... 607/57 |
| 2009/0254150 A1 | 10/2009 | Zierhofer ........................ 607/57 |

OTHER PUBLICATIONS

Wilson, et al, "Better Speech Recognition With Cochlear Implants", *Nature*, vol. 352, Jul. 18, 1991, pp. 236-238.
(Continued)

*Primary Examiner* — Carl H Layno
*Assistant Examiner* — Jon Eric C Morales
(74) *Attorney, Agent, or Firm* — Sunstein Kann Murphy & Timbers LLP

(57) ABSTRACT

A method is described for generating stimulus signals for an auditory prosthesis system. A high frequency signal conveys higher frequency audio information including exceptionally low rate band-pass envelope characteristics. This high frequency signal represents at least the upper part if not all of the range of frequencies for speech, music, and other sounds that are audible to listeners with normal hearing. A separate low frequency signal is also provided representing lower audio frequency information including periodicity characteristics (voiced/unvoiced or periodic/aperiodic distinctions) and for periodic sounds, fundamental frequency characteristics. The high frequency signal is applied to the auditory system of a patient by an associated high frequency stimulator, and the low frequency signal is applied to the auditory system of the patient by an associated low frequency signal.

18 Claims, 5 Drawing Sheets

(56) References Cited

OTHER PUBLICATIONS

Wilson, et al, "Temporal Representations With Cochlear Implants", *The American Journal of Otology*, vol. 18 No. 6(Suppl), 1997, pp. S30-S34.

International Searching Authority, Officer Blaine R. Copenheaver, International Search Report and Written Opinion, PCT/US2010/048350, dated Oct. 27, 2010.

* cited by examiner

LOW PULSE RATE COCHLEAR IMPLANT STIMULATION IN CONJUNCTION WITH A SEPARATE REPRESENTATION OF FUNDAMENTAL FREQUENCIES AND VOICED/UNVOICED DISTINCTIONS

This application claims priority from U.S. Provisional Patent Application 61/241,438, filed Sep. 11, 2009, which is incorporated herein by reference.

FIELD OF THE INVENTION

The present invention relates to medical implants, and more specifically to electric and acoustic stimulation techniques in cochlear implant systems and other implantable auditory prostheses.

BACKGROUND ART

Speech sounds can be characterized as voiced or unvoiced. Vowel sounds are examples of voiced speech sounds which are formed by the vocal cords vibrating to produce a periodic signal containing multiple harmonic frequency components. The lowest frequency component in such a signal is referred to as the fundamental frequency, $f_0$. In the voiced speech of adult males, the fundamental frequency falls between about 85-155 Hz. In adult females, the fundamental frequency of voiced speech is a bit higher, typically from around 165-255 Hz. Besides voiced speech, many speech sounds such as consonant sounds are aperiodic, referred to as unvoiced. The term "voicing" is used herein to refer to information related to voiced/unvoiced speech characteristics.

A human ear normally transmits sounds such as speech sounds as shown in FIG. 1 through the outer ear 101 to the tympanic membrane (eardrum) 102, which moves the bones of the middle ear 103 (malleus, incus, and stapes) that vibrate the oval window membrane of the cochlea 104. The cochlea 104 is a long narrow duct wound spirally about its axis for approximately two and three quarters turns. It includes three chambers along its length: an upper chamber known as the scala vestibuli, a middle chamber known as the scala media, and a lower chamber known as the scala tympani. The cochlea 104 forms an upright spiraling cone with a center called the modiolus where the axons of the auditory nerve 113 reside. These axons project in one direction to the cochlear nucleus in the brainstem and they project in the other direction to the spiral ganglion cells and neural processes peripheral to the cells (hereinafter called peripheral processes) in the cochlea. In response to received sounds transmitted by the middle ear 103, sensory hair cells in the cochlea 104 function as transducers to convert mechanical motion and energy into electrical discharges in the auditory nerve 113. These discharges are conveyed to the cochlear nucleus and patterns of induced neural activity in the nucleus are then conveyed to other structures in the brain for further auditory processing and perception.

Hearing is impaired when there are problems in the ability to transmit sound from the external to the inner ears or problems in the transducer function within the inner ear. To improve impaired hearing, auditory prostheses have been developed. For example, when the impairment is related to the operation of the middle ear 103, a conventional hearing aid may be used to provide acoustic stimulation to the auditory system in the form of amplified sound. Or when the impairment is associated with the transducer function in the cochlea 104, a cochlear implant can electrically stimulate auditory nerve tissue with small currents delivered by multiple electrode contacts distributed along at least a part of the cochlear length (spiral). Arrays of such electrodes normally are inserted into the scala tympani. Alternatively, groups of auditory nerve axons can be stimulated with electrodes placed within the modiolus, or auditory structures in the brain can be stimulated with electrodes placed on or within the structures, for example, on or within the cochlear nucleus.

FIG. 1 also shows some components of a typical auditory prosthesis system for combined electric and acoustic stimulation (EAS) of the cochlea 104. The system includes an external microphone that provides an audio signal input to an external signal processor 111 where various signal processing schemes can be implemented. In an EAS system, there are two different signal processing paths. An acoustic stimulation signal is produced by the external processor 111 and delivered to an acoustic stimulation module such as a conventional hearing aid transducer 105 in the ear canal which acoustically stimulates the tympanic membrane 102, driving the bones of the middle ear 103, which mechanically stimulate the cochlea 104. In addition, the external signal processor 111 derives patterns of electrical stimuli from the audio signal input and converts these patterns into a digital data format, such as a sequence of data frames, for transmission from an external transmitter coil 107 to an implanted receiver coil 106. The receiver coil 106 delivers the received data signals to an implanted receiver/stimulator module 108. Besides receiving the processed audio information, the receiver/stimulator 108 also performs additional signal processing such as error correction, pulse formation, etc., and produces electrical stimuli (based on the received data signals) that are sent through an electrode lead 109 to stimulation electrodes in an implanted array of electrodes (hereinafter called the electrode array) 110 to provide selective electrical stimulation of the auditory nerve 113. The electrode array also can be placed at more central sites in the ascending auditory pathway, for example, within the auditory nerve in the modiolus rather than within the cochlea, or on or within the cochlear nucleus or the inferior colliculus. In these cases, the array may have a different geometric configuration, number of contacts, and distribution of contacts compared with an array used for implantation into the cochlea.

At present, the most successful electrical stimulation strategy for implantable auditory prostheses is the so called "continuous interleaved sampling" (CIS) strategy introduced by Wilson B S, Finley C C, Lawson D T, Wolford R D, Eddington D K, Rabinowitz W M, "Better Speech Recognition with Cochlear Implants," Nature, vol. 352, 236-238, July 1991, which is incorporated herein by reference. Signal processing for CIS in the speech processor typically involves the following steps: (1) splitting up of the audio frequency range into spectral bands by means of a filter bank; (2) envelope detection of each filter output signal; (3) instantaneous nonlinear compression of the envelope signal (map law); and (4) modulation of a pulse train for each electrode with the compressed envelope signal for the corresponding band-pass channel.

FIG. 2 shows various functional blocks in a typical CIS processing system. FIG. 3 shows an example of a short time period of an audio speech signal from a microphone or the like, which is input to a pre-emphasis filter 201 which attenuates strong frequency components in the signal below about 1.2 kHz. Following the pre-emphasis filter 201 are multiple band-pass filters (BPFs) 202 which decompose the speech signal or other audio input from the pre-emphasis filter into multiple spectral bands as shown, for example, in FIG. 4. Envelope detectors 203 extract the slowly-varying envelopes of the spectral band signals, for example, by full-wave rectification and low pass filtering. Compression of the envelopes is performed by non-linear (e.g., logarithmic) mapping 204 to fit the patient's perceptual characteristics, and the compressed envelope signals are then multiplied with carrier waveforms by modulators 205 to produce non-overlapping biphasic output pulses for the stimulation electrodes (EL-1 to EL-n) implanted in the cochlea, or in the modiolus, or on or within an auditory structure in the brain. The blocks preceding each electrode, blocks 202, 203, 204, and 205, are alternatively called a channel, a signal channel, or a stimulation channel.

SUMMARY OF THE INVENTION

Embodiments of the present invention are directed to a method for generating audio signals for an auditory prosthesis system. A high frequency signal conveys higher frequency audio information including exceptionally low rate band-pass envelope characteristics. This high frequency signal represents at least the upper part if not all of the range of frequencies for speech, music, and other sounds that are audible to listeners with normal hearing. A separate low frequency signal is also provided representing lower audio frequency information including periodicity characteristics (voiced/unvoiced or periodic/aperiodic distinctions) and for periodic sounds, fundamental frequency characteristics. The high frequency signal is applied to the auditory system of a patient by an associated high frequency stimulator, and the low frequency signal is applied to the auditory system of the patient by an associated low frequency stimulator.

In further specific embodiments, the high frequency signal stimulator may include a cochlear implant electrode array having high frequency stimulation electrodes for applying the high frequency stimulation signal to nearby neural tissue. The high frequency signal may be applied to the high frequency stimulation electrodes as a sequence of electric pulses at a pulse rate of less than 100 Hz. The cochlear implant electrode array may contain more than 12 stimulation electrodes, for example, at least 16 stimulation electrodes.

The part of the system for the separate representation of the lower frequencies in the audible spectrum may include separate electrodes in the electrode array that are distinct from the electrodes used to represent the higher frequencies in the audible spectrum. For example, the electrodes for representing the lower frequencies may be closer to the apical end of the electrode array than are the electrodes for representing the higher frequencies. The representation of the lower part of the audible spectrum may be based on (1) a Fine Structure Processing (FSP) strategy, as described by Hochmair I, Nopp P, Jolly C, Schmidt M, Schößer H, Garnham C, Anderson I, "MED-EL Cochlear Implants: State of the Art and a Glimpse into the Future," Trends in Amplification, vol. 10, 201-219, 2006, which is incorporated herein by reference; (2) a CIS strategy; and/or (3) one or more channel balance cues. In the cases of separate representations of the higher and lower frequencies, the dividing line is at about 300 Hz, for example, frequencies between 300 and 7000 Hz would be represented with the low-rate electric pulses and frequencies between 70 and 300 Hz, and/or features of frequency variations in that range, would be represented in some other way. The 70-300 Hz range of frequencies includes the fundamental frequencies of man, woman, and child talkers as well as the fundamental frequencies of many musical and environmental sounds.

In some embodiments, the low frequency stimulator may include an acoustic-mechanical stimulation module for applying the low frequency signal as an acoustic-mechanical input directed to the middle ear of the patient. For example, the acoustic-mechanical stimulation module may be a conventional hearing aid, a middle ear implant, an electro-mechanical transducer for stimulating the round window membrane of the cochlea or of the fluid of the inner ear (see, e.g., US Patent Publication 2008064918, which is incorporated herein by reference), or by vibrational stimulation of cerebral fluid or cerebral structures (see, e.g., US Patent Publication 2008039771, which is incorporated herein by reference), or the acoustic stimulation part of devices specifically designed for combined EAS of the auditory system (such as described in U.S. Pat. No. 6,231,604, which is incorporated herein by reference). In these embodiments, the acoustic stimuli would excite the remaining residual low-frequency hearing of the patient. The acoustic stimuli can be delivered to either ear or to both ears; in cases of acoustic stimulation of one ear only, the ear with the better residual hearing would be preferred. In addition, frequencies higher than 300 Hz may be represented in the stimuli if the residual hearing of the patient is sensitive to frequencies above 300 Hz. Such embodiments utilizing an acoustic stimulation module would not be useful for persons with no remaining hearing and therefore alternative embodiments may be useful for those persons. In further specific embodiments, the high frequency signal may include an anti-hum jitter component.

DETAILED DESCRIPTION OF SPECIFIC EMBODIMENTS

Figure 1:
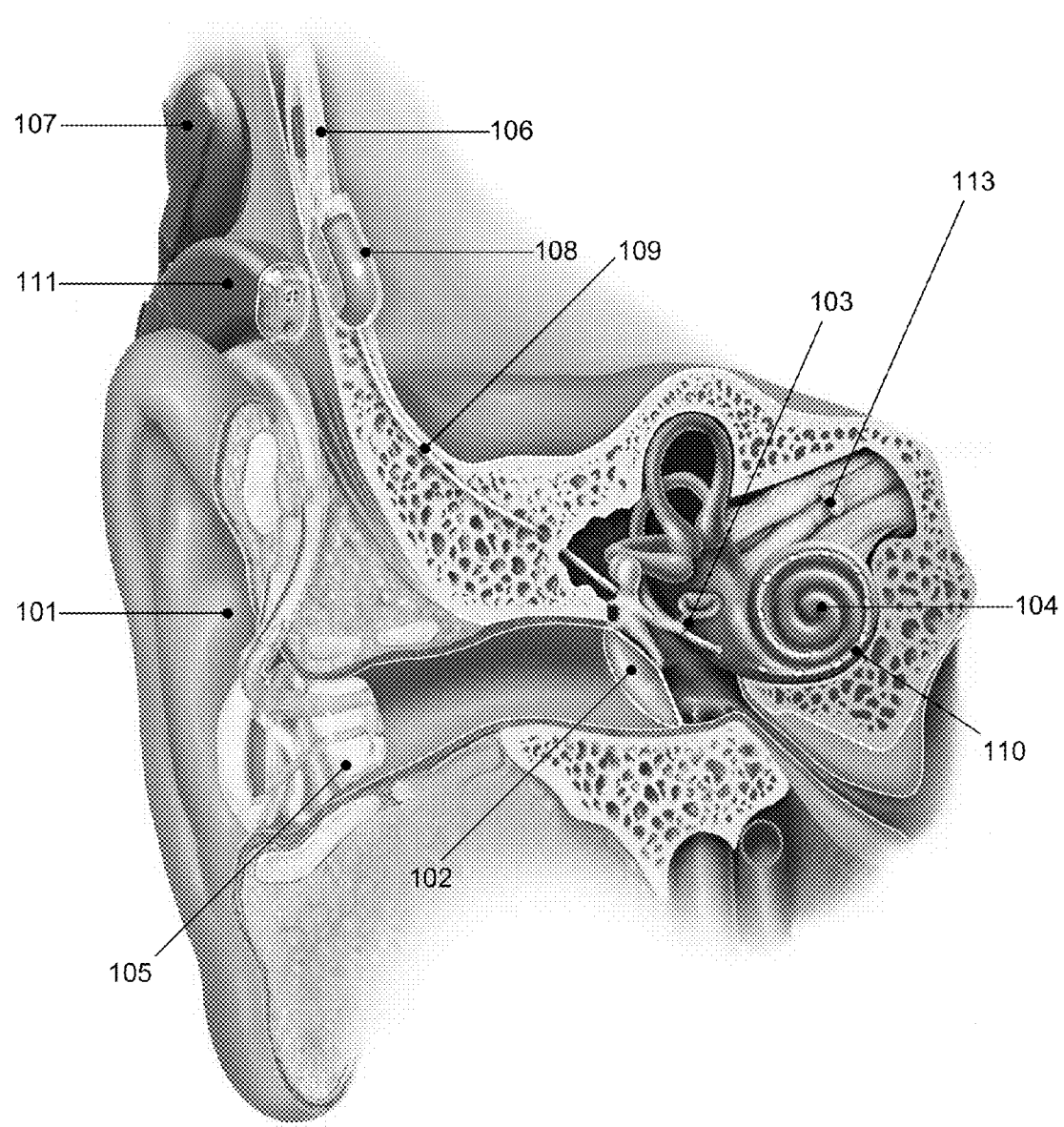
FIG. 1 shows a section view of a human ear with a typical auditory prosthesis system designed to deliver electric stimuli to the inner ear and acoustic stimuli at the ear canal.

It would be useful for an auditory prosthesis to present electric stimulation pulses at very low rates for many or all of the signal channels and associated stimulation electrodes. That would reduce electrode interactions and improve modulation detection. Most of the information in speech, except for fundamental frequency and voicing information (voiced/unvoiced, or more broadly, periodic/aperiodic) is conveyed by signal modulations at and below about 16 Hz, for each of multiple frequency bands in the audible spectrum. For example, see Xu L, Zheng Y, "Spectral and Temporal Cues for Phoneme Recognition in Noise," J. Acoust. Soc. Am., vol. 122, 1758-1764, 2007, which is incorporated herein by reference. Using the 4× oversampling rule (as described for example by Wilson B S, Finley C C, Lawson D T, Zerbi M, "Temporal Representations with Cochlear Implants," Am. J. Otol., vol. 18, S30-S34, 1997; incorporated herein by reference), this means that pulse rates theoretically could be as low as 64 pulses/s/electrode for representing these essential modulations below 16 Hz using the CIS or other strategies. Alternatively, even lower rates may also be highly effective. For example, 32 pulses/s/electrode would still provide a 2× oversampling as specified by the Nyquist theorem and therefore may be effective in representing modulations below 16 Hz. In addition, the sensitivity to modulation may be higher with the 32 pulses/s/electrode rate as compared to the sensitivity with the 64 pulses/s/electrode rate. Thus, rates as low as 64 pulses/s/electrode would be highly conservative choices for the present invention, but even lower rates, down to as low as 32 pulses/s/electrode, may be similarly or even more effective. These stimulation rates, down to as low as 32 pulses/s/electrode, are much lower than the stimulation rates used in conventional cochlear implant systems.

The exceptionally low pulse rates are possible when the fundamental frequency and periodicity information are represented in some other way than by using high cutoff frequencies for the envelope detectors in the signal channels. For example, the acoustic stimulation module of a combined EAS system may provide an excellent representation of fundamental frequency and the first one or two harmonics along with periodicity distinctions (voiced/unvoiced). In that case, the cochlear implant portion of the EAS system could use very low pulse rates for the stimulation electrodes, and the fundamental frequency and periodicity information would be provided by the acoustic stimulus signal and residual hearing.

Thus, embodiments of the present invention are directed at providing separate stimulation mechanisms for (1) the lower frequencies in the audible spectrum including fundamental frequency and periodicity (voiced/unvoiced) information using various multiple processing approaches and stimulus modes, and (2) the higher frequencies in the audible spectrum using electric stimuli at exceptionally low stimulation rates. The very low stimulation rates provide reduced electrode interactions and a greater sensitivity to modulation compared with conventional (higher) rates. These advantages are highly likely to translate to a better perception of speech and other sounds for users of implantable auditory prostheses.

Figure 3:
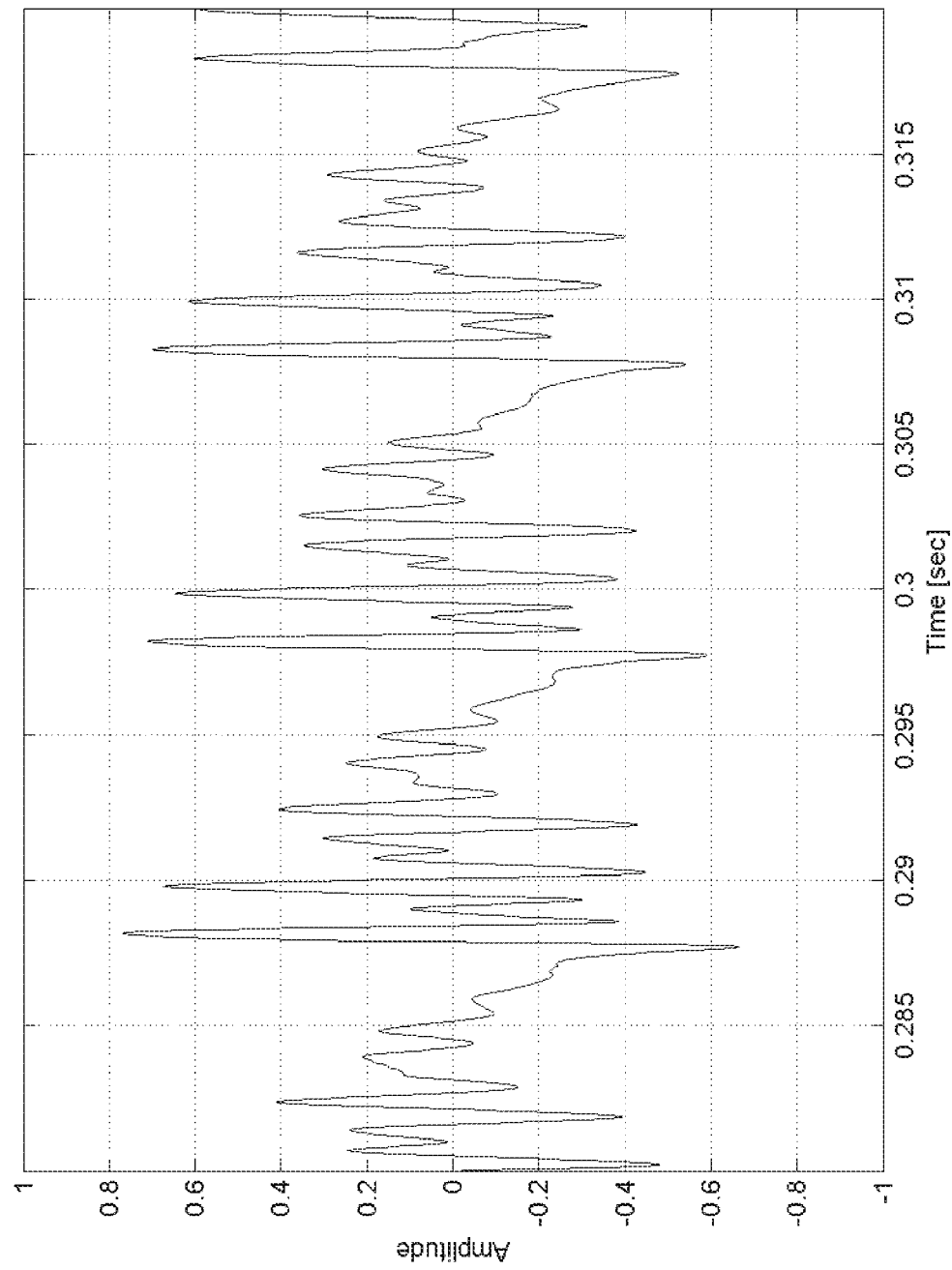
FIG. 3 shows an example of a short time period of an audio speech signal from a microphone.
Figure 4:
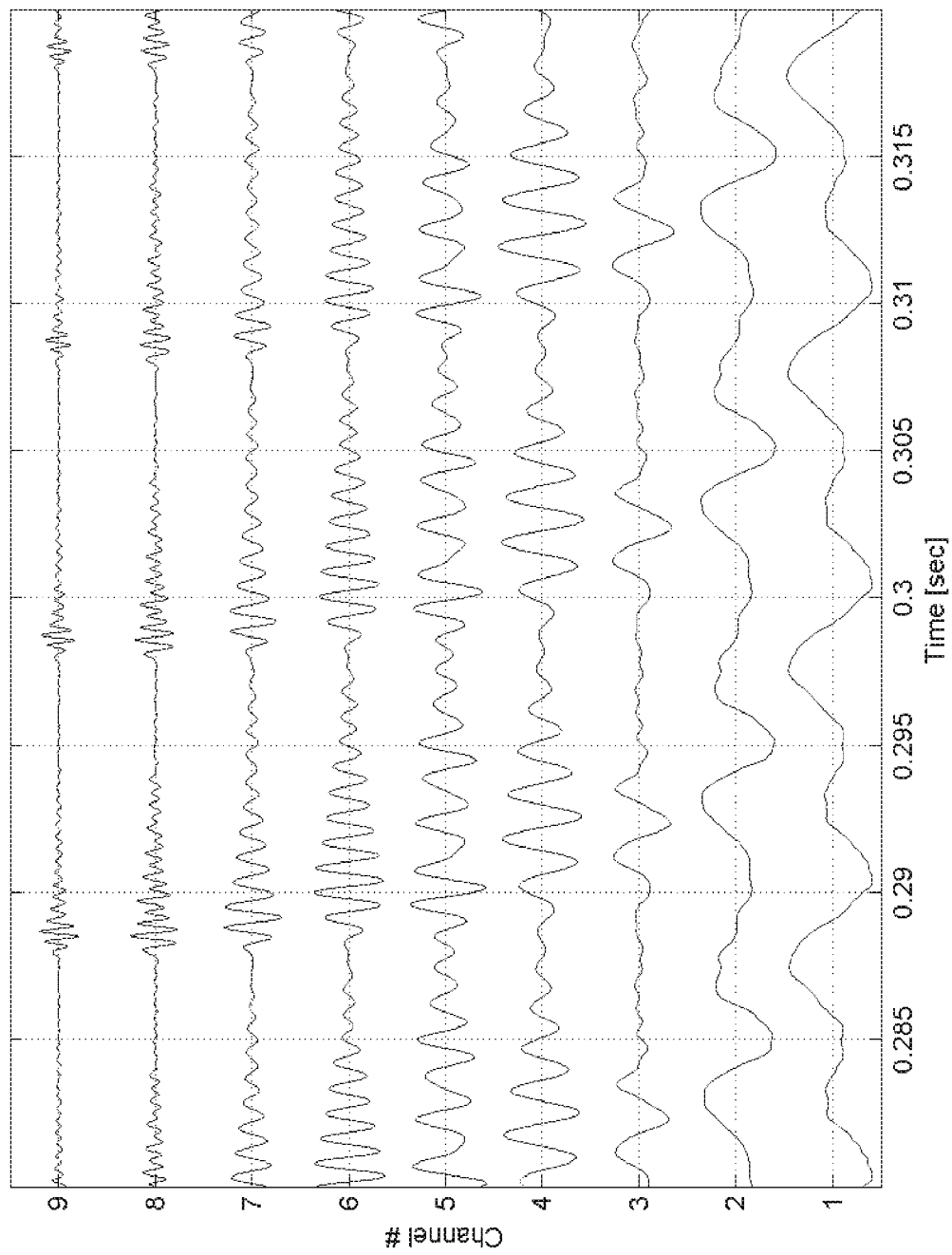
FIG. 4 shows an acoustic microphone signal decomposed by band-pass filtering by a bank of filters into a set of signals.
Figure 5:
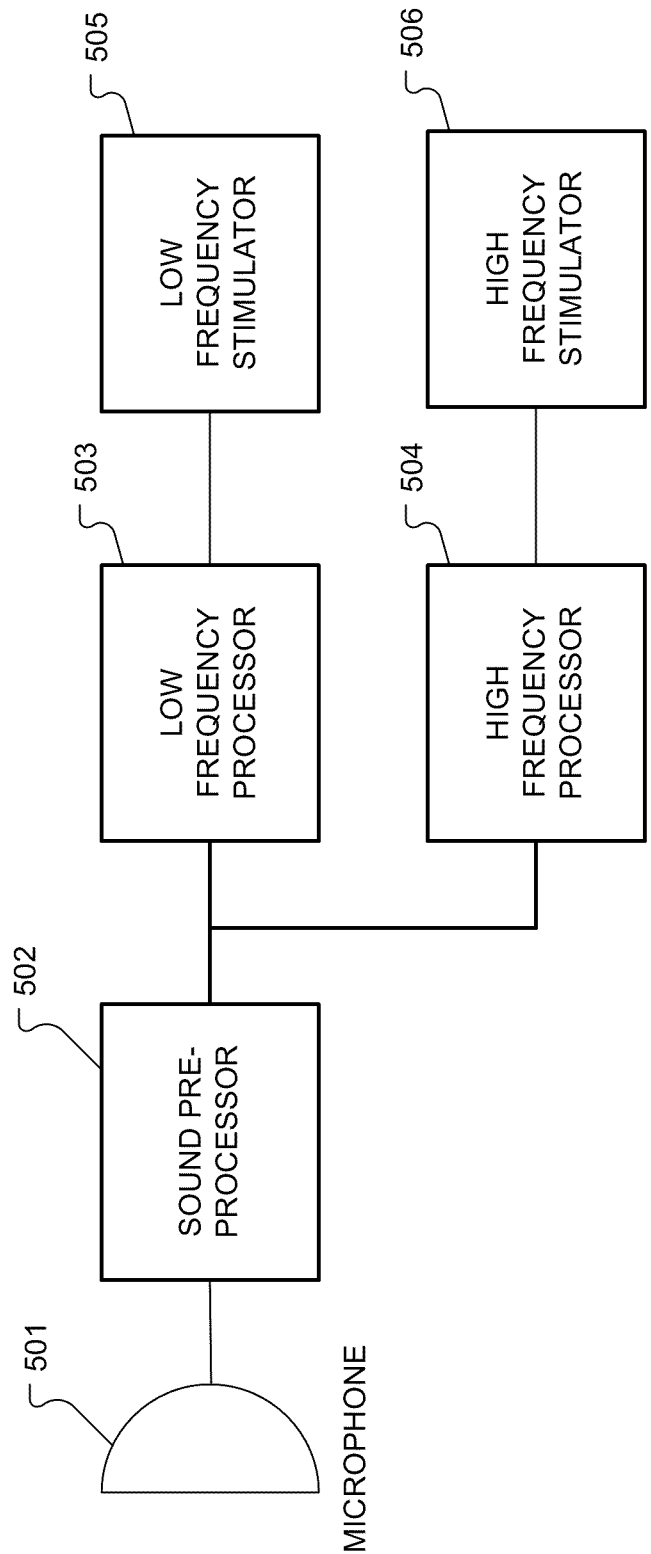
FIG. 5 shows various functional blocks in one generic embodiment of the present invention.

FIG. 5 shows various functional blocks in one generic embodiment of the present invention, which may include components such as the ones shown in FIG. 1 for combined EAS of the auditory system. A sensing microphone 501 (e.g., in an external processor 111) initially senses incoming acoustic signals to generate a representative audio microphone signal such as the one shown in FIG. 3. The external processor 111 may also contain a sound pre-processor 502 that analyzes the audio microphone signal to form a pre-processed audio signal. A low frequency processor 503 (e.g., in the external processor 111) processes lower frequency portions of the audio signal (e.g., for frequencies below about 300 Hz) to produce a representation of the lower audio frequency information including periodicity and fundamental frequency characteristics. An associated low frequency stimulator 505 delivers this low frequency signal to the auditory system of the patient. For example, the low frequency stimulator 505 may be the acoustic stimulator 105 of a combined EAS prosthesis system, or it may be a subset of the stimulation electrodes in a cochlear implant electrode array 110, which may include only one or a few of the electrodes in the array such as one or two of the most apical electrodes.

Figure 2:
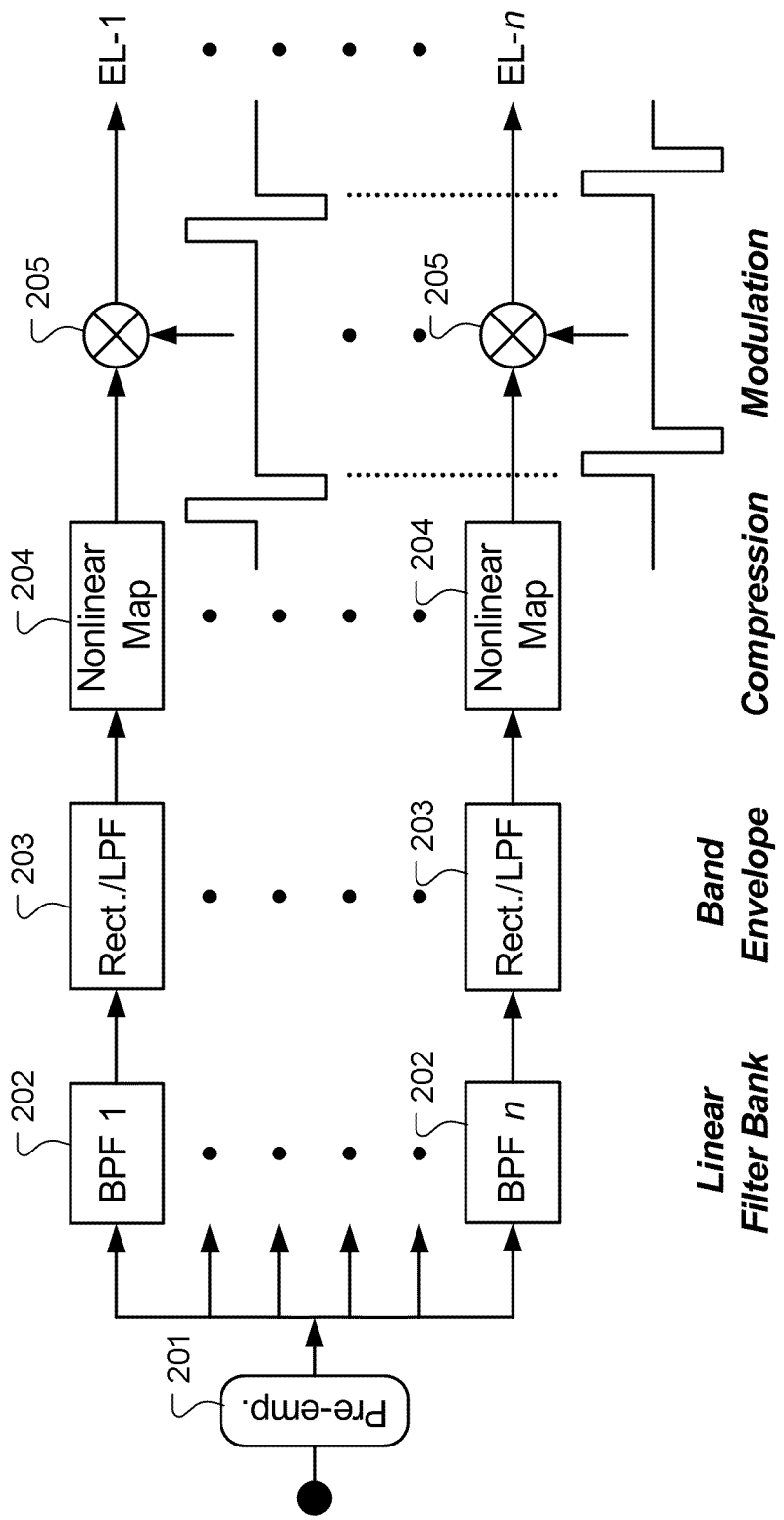
FIG. 2 shows various functional blocks in a continuous interleaved sampling (CIS) processing system.

Another high frequency processor 504 processes higher frequency portions of the audio signal (e.g., for frequencies above about 300 Hz) to produce a representation of the higher audio frequency information including band-pass envelope characteristics. This may be based on CIS (FIG. 2) or other signal processing strategies for cochlear implants. It may be helpful to use exceptionally low cutoff frequencies for the low-pass filters in the envelope detectors for those strategies, for example, for the low-pass filters in the envelope detectors for the CIS strategy 203. An associated high frequency stimulator 506 delivers this high frequency stimulation signal to the auditory system of the patient. For example, the high frequency stimulator 506 may be a cochlear implant electrode array 110 having multiple stimulation electrodes, each of which stimulates nearby neural tissue in the specific form of a sequence of electric pulses at a low pulse rate of about 100 pulses/s/electrode or even lower, for example, 64 pulses/s/electrode. In some embodiments, all of the electrodes in the array may be used for the high frequency stimulator 506, while in other embodiments, most of the electrodes in the array may be used for this purpose. In some further embodiments, the processor functions may be physically separated in different ways than as given above, or they may be combined in a single housing or a single device.

For cochlear implant patients who retain some residual hearing, the low frequency stimulator 505 may be an acoustic stimulation module such as a conventional hearing aid, a middle ear implant which applies the stimulus as an acoustic input directed to the middle ear, or the acoustic stimulation part of devices specifically designed for combined EAS of the auditory system 105. Use of an acoustic stimulator for conveying the representation of frequencies below about 300 Hz allows all the cochlear implant stimulation channels to be treated in the same way, because all of those channels and associated electrodes can be dedicated to providing the representation of frequencies above about 300 Hz, as provided by the high frequency stimulator 506. This simplifies system design and also may simplify the percepts elicited by the electric stimuli.

For patients who do not have useful residual hearing (and very little may be needed—see, for example, Dorman M F, Gifford R H, Spahr A J, McKarns S A, "The Benefits of Combining Acoustic and Electric Stimulation for the Recognition of Speech, Voice and Melodies," Audiology & Neuro-Otology, vol. 13, 105-112, February 2008; incorporated herein by reference), the low frequency stimulator 505 may be based on using one or more electrodes in the cochlear implant electrode array 110, which are separate from the high frequency stimulation electrodes associated with the high frequency stimulator 506. For example, the one or more low frequency electrodes may be 1-3 electrodes which are closer to an apical end of the electrode array than are the other high frequency stimulation electrodes in the array, which would remain available for the very low rate stimulation strategy described above as implemented by the high frequency stimulator 506. In such an embodiment, the representation of frequencies below about 300 Hz may be based on various stimulation strategies and mechanisms such as a Continuous Interleaved Sampling (CIS) strategy or Fine Structure Processing (FSP). Other embodiments may be based on other representations of fundamental frequency during voiced intervals at the most apical electrodes, for example, an additional deep modulation at the fundamental frequency rate as described in Geurts L, Wouters J, "Coding of Fundamental Frequency in Continuous Interleaved Sampling Processors for Cochlear Implants," J. Acoust. Soc. Am., vol. 109, 713-726, 2001, which is incorporated herein by reference.

There may be other viable approaches for providing a representation of lower audio frequencies which may include a fundamental frequency signal and/or indications of periodic/aperiodic (voiced/unvoiced) distinctions. For example, presentation of pulses (or sequences of pulses) on the apical-most electrode at rates equal or proportional to the instantaneous fundamental frequency during voiced speech intervals, along with presentation during unvoiced speech intervals of (1) the lower-rate pulses (as used for the other electrodes), (2) pulses presented at random intervals, or (3) pulses presented at a fixed rate above the so-called pitch saturation limit of about 300 pulses/s or somewhat higher for most cochlear implant patients. Such an arrangement might be based on using fundamental frequency and voiced/unvoiced detectors as parts of the auditory prosthesis system. Alternatively, standard cutoff frequencies for the envelope detectors, and standard rates of stimulation, can be used for the most-apical (lowest center frequency for the BPFs) one or two channels, as in CIS and other approaches. Then the exceptionally low cutoffs for the envelope detectors, and the exceptionally low rates of stimulation, can be used for the remaining channels. With this approach, fundamental frequency variations and voiced/unvoiced distinctions would be represented in the normal way at the apical-most electrode or electrodes, that is, through variations in the mapped modulation signal (one of the inputs to the modulators 205) that include variations up to the cutoff frequency of envelope detector(s) for those channel(s), typically 200-400 Hz.

Another embodiment may be based on use of low stimulation rates throughout, but with extension of the frequency range spanned by the band-pass filters 202 downward to around 70 Hz so as to include a full range of fundamental frequencies (including the fundamental frequencies for adult males with low-pitched voices). This may allow fundamental frequency to be conveyed based on a channel balance cue, and also provide a representation of fine frequency variations throughout the spectrum, especially if band-pass filters with triangular- or bell-shaped frequency responses are used and/or if pairs of adjacent electrodes are stimulated sequentially so as to enhance the perceptual salience of the channel-balance cues. In this embodiment, the separate processing and stimulation functions for the representation of lower audio frequencies (e.g., below about 300 Hz—as processed by the low frequency processor 503 and presented by the low frequency stimulator 505 in FIG. 5) are not needed and may not be required.

Progressive improvements in reducing electrode interactions and in increasing the sensitivity to modulation should be produced with progressive reductions in the pulse rate for the electrical stimuli delivered through the implant and concomitant increases in the time interval between pulses at sequentially stimulated electrodes. For example, modulation sensitivity is much better at 250 pulses/s/electrode than at 4000 pulses/s/electrode. Electrode interactions also are eliminated or negligible with a time separation of 640 microseconds between sequentially stimulated electrodes, at least for stimulation through a cochlear implant and probably also for electrical stimulation at more central sites in the ascending auditory pathway.

As previously explained, the theoretical lowest rate on any single electrode that certainly can support an undistorted representation of the essential modulation frequencies up to 16 Hz is 64 pulses/s. For a 12-electrode implant using 50 microsecond pulses (25 microseconds/phase), this rate would produce a 1.252 ms interval between sequentially stimulated electrodes, which is far in excess of the 640 microsecond interval required to eliminate all measurable electrode interactions in the study of Bierer J A, Middlebrooks J C, "Cortical Responses to Cochlear Implant Stimulation: Channel Interactions," J. Assoc. Res. Otolaryngol., vol. 5, 32-48, 2004, which is incorporated herein by reference. In addition, the pulse rate also is far below the 250 pulses/s/electrode required for relatively good sensitivity to modulation, as described for example in Pfingst B E, Xu L, Thompson C S, "Effects of Carrier Pulse Rate and Stimulation on Modulation Detection by Subjects with Cochlear Implants," J. Acoust. Soc. Am., vol. 121, 2236-2246, 2007, which is incorporated herein by reference. This example using 12 electrodes and 50 microsecond pulses indicates that either a higher number of electrodes, or pulses with greater durations, or both, could be used and still not produce an interval between sequentially stimulated electrodes that is less than 640 microseconds. For example, a 16-electrode implant and 100 microsecond pulses would produce an interval of 877 microseconds, still well in excess of 640 microseconds. It is possible that the sensitivity to modulation for the 64 pulses/s/electrode rate is better than the sensitivity for the previously-tested 250 pulses/s/electrode rate. This could be evaluated and if no further gains in sensitivity are found with the reduction in stimulation rate from 250 to 64 pulses/s/electrode, then higher rates—up to 250 pulses/s/electrode—could be used without harm and without producing intervals between sequentially stimulated electrodes that are less than 640 microseconds for many combinations of pulse durations and numbers of electrodes in the implant. But this is an unlikely outcome given the monotonic behavior of the prior data, and 64 pulses/s/electrode may well support better sensitivity to modulation than 250 pulses/s/electrode. In the absence of further data, the default rate should be 64 pulses/s/electrode.

As also previously explained, stimulation rates as low as 32 pulses/s/electrode also may be highly effective. Use of such lower stimulation rates would allow an even higher number of electrodes, or pulses with even greater durations, or both, without producing an interval between sequentially stimulated electrodes that is less than 640 microseconds.

In addition to the low pulse rates and the concomitant long time intervals between sequentially stimulated electrodes, further gains may be produced in the representation of the frequencies above about 300 Hz by using ideal or nearly ideal shapes for the band-pass filter frequency responses. This produces a channel balance cue that can signal to an implant patient the presence of a frequency that is intermediate to the two center frequencies of the band-pass filters for adjacent channels in the implant processing strategy.

It also may be beneficial to use sequential stimulation for each pair of all pairs of adjacent or tonotopically ordered electrodes in the implant. This assures that the spatial distance between sequentially stimulated electrodes does not exceed a 3 mm maximum for a clear and unambiguous perception of the channel balance cue (see McDermott H J, McKay C M, "Pitch Ranking with Non-Simultaneous Dual Electrode Electrical Stimulation of the Cochlea," J. Acoust. Soc. Am., vol. 96, 155-162, 1994; incorporated herein by reference). For example, one standard distance between electrodes in cochlear implant electrode arrays is 2.4 mm. An update order other than the ones indicated above would impose distances of 4.8 mm and higher for at least some of the sequentially stimulated electrodes which would exceed the maximum 3 mm spatial separation distance for the clear and unambiguous perception.

It also may be useful to preserve the ratio of the (unmapped) envelope signals for the adjacent channels (in terms of the center frequencies for the band-pass filters in each of the channels) in the amplitudes of the pulses that are delivered to the associated electrodes. This would represent the channel balance cue without the distortion that otherwise would be produced with the non-linear mapping function normally used for each channel, so as to map the wide dynamic range of envelope variations onto the narrow dynamic range of electrically evoked hearing. For the present approach to processing for cochlear implants (or for implants at more central sites in the ascending auditory system), a non-linear transformation would be applied for adjacent channels together to perform the necessary mapping while still preserving the relative amplitudes of the pulses for the two channels and associated electrodes.

One possible concern with relatively long time intervals between sequentially stimulated electrodes is that accurate perception of the channel balance cue may require that stimulation pulses be presented to the two electrodes (for each sequential pair) within some maximum time interval, as well as within the maximum distance between the two electrodes (e.g., approximately 3 mm) Studies have been performed using a fixed time interval of 400 microseconds and up to 6.7 ms which showed that the channel balance cue could be perceived and utilized by cochlear implant subjects, including the use of the relatively long time intervals between sequentially stimulated electrodes. Another study measured pitch discrimination for sequentially interleaved pulse trains to adjacent electrodes in a Nucleus 24 cochlear implant electrode array with time offsets between the trains of 500, 1000, 1500, and 2000 microseconds. It was found that intermediate pitches—between the pitches elicited with stimulation of either electrode in the pair alone—varied with the ratio of the pulse amplitudes for the two electrodes with the 500 and 1000 microsecond time offsets. More complicated percepts were sometimes elicited with the larger time offsets. It was thus recommended to use time offsets of 1000 microseconds or less for the reliable control and production of intermediate pitches (and by implication the reliable representation of channel balance cues). The present invention may use any time interval between sequentially stimulated electrodes that allows for accurate perception of the channel balance cue. The existing literature indicates that this interval may be as long as 6.7 ms or even longer, and the literature includes a recommendation that the intervals should be about 1000 microseconds or shorter. The intervals specified in the examples above, 1252 and 877 microseconds, are within the range of this recommendation. However, even longer intervals—up to and perhaps beyond 6.7 ms—may also allow for accurate perception of the channel balance cue.

Another possible concern is that the use of a fixed low rate of pulse presentations for all or most channels in the implant may produce a perception of a low-frequency "hum" or "buzz" corresponding to the rate. One approach for addressing this potential problem is to randomize the timing of the pulse presentations within and across channels (an anti-hum jitter component) which might eliminate or at least substantially reduce the unwanted percept if present. A possible downside to this approach is that it would require an increase in the average rate of stimulation at each electrode, as the minimum (instantaneous) rate should be no lower than 32 or 64 Hz, for the reasons discussed above. However, the average rate could be increased for many combinations of pulse durations and numbers of electrodes in the implant while still preserving a minimum time interval of 640 microseconds between sequentially stimulated electrodes and while still not exceeding the 250 pulses/s/electrode rate for good sensitivity to modulation. For example, for a 12-channel implant and 50 microsecond pulses, instantaneous rates at any electrode could range between 64 and 250 pulses/s without exceeding the 250 pulses/s/electrode rate and without producing a time interval between sequentially stimulated electrodes of less than 640 microseconds. This range of rates (and the concomitant increase in the average rate at any one electrode) would be entirely sufficient for randomizing pulse presentation times and abolishing any hum or buzz percepts.

A further advantage of the low pulse rate strategies discussed above is that the implant system power consumption is greatly reduced. That means that existing implant batteries as used with external speech processors would last longer, and that making fully implantable systems would be more feasible.

In addition, low-rate strategies make available considerable time between the stimulus onsets for sequentially stimulated electrodes, and this may allow the use of special stimulus waveforms such as long-duration pulses, asymmetric pulses, split-phase pulses, triphasic pulses, or pseudo-monophasic pulses. At least some of these waveforms (e.g., asymmetric and pseudo-monophasic pulses) would certainly reduce the currents needed for threshold and comfortably loud auditory percepts compared to short-duration biphasic pulses as are used in existing implant systems. This would further reduce power consumption in addition to the power savings already realized from the low stimulation rates. Alternative waveforms may also confer other advantages as well, including one or more of the following: (1) an increase in the dynamic range of electrical stimulation from threshold to comfortably loud percepts, (2) an even further reduction in electrode interactions, and (3) selective activation of neural processes peripheral to the spiral ganglion cells at cochlear locations where peripheral processes are present.

An embodiment of an auditory prosthesis may also include use of deeply-inserted electrode arrays for complete cochlear coverage (at least for patients who do not have any useful residual hearing in an ear to be implanted). Larger numbers of electrode sites (e.g., 12 or more) may also be helpful when electrode interactions are substantially reduced with the low-rate stimuli, and when the implant design is tailored to enhance the representation of channel balance cues, across adjacent electrode positions. With the reduction in electrode interactions (and perhaps central interactions as well), a greater number of effective channels may be available with cochlear implants (e.g., more than the 4-8 effective channels obtained with conventional implant systems). If so, the number of stimulation electrodes should at least match the number of effective channels.

The low stimulation rates and corresponding long times between channel updates also may offer special opportunities to stimulate selectively any remaining peripheral processes, for example, with long-duration pulses. The shapes, latencies, and amplitudes of intra-cochlear evoked potentials to certain stimuli can be used to determine whether the processes are present. And when the processes are present, certain stimuli such as long-duration pulses or ramped or exponentially-rising stimuli may excite the processes exclusively or preferentially compared to excitation at more central sites, for example, at the spiral ganglion cells. Also, certain configurations of intra-cochlear electrodes may be useful in exciting the peripheral processes instead of the ganglion cells or central axons.

Selective activation of peripheral processes when they are present may well produce a further improvement in the performance of cochlear implants. (Such activation would not be applicable for auditory prostheses that present electrical stimuli within the auditory nerve in the modiolus or at sites in the ascending auditory pathway central to the auditory nerve.) For example, increases in the dynamic range and spatial specificity of stimulation are likely with such activation, and those increases are in turn likely to produce salutary effects on speech and music reception. Selective activation of peripheral processes may be made possible with the greater amount of time available for stimulus waveforms in the described auditory prosthesis systems using exceptionally low rates of stimulation.

The low stimulation rate strategies described herein may increase the number of effective channels that can be used with cochlear implants or other auditory prostheses. This can be explicitly determined by measuring speech reception with increasing numbers of channels (and the associated stimulation electrodes) until the scores do not increase with further increases in the numbers of channels, as has been done before with other processing strategies, for example, the CIS and spectral peak (SPEAK) strategies. Results obtained with the low stimulation rate strategies should be compared directly in the same study with results obtained with a control strategy, for example, CIS using conventional cutoff frequencies for the low-pass filters in the envelope detectors and conventional rates of stimulation at the electrodes.

A further embodiment of an auditory prosthesis may also include the use of optical rather than electrical stimuli for the high frequency stimulator 506. Indeed, the exceptionally low pulse rates specified in this invention for that stimulator may allow optical stimuli to become effective for an auditory prosthesis, in that only low rates, below or well below 70-100 optical pulses/s/stimulation site, may be safely or practically applied for presently envisioned systems for optical stimulation (see e.g., Rajguru S M, et al., *Optical Cochlear Implants: Evaluation of Surgical Approach and Laser Parameters in Cats*, Hear. Res., epub ahead of print, doi:10.1016/j.heares.2010.06.021; incorporated herein by reference). So for example, embodiments of the invention could be in the form of a combined optical/electrical/acoustic system (e.g. optical stimulation for high frequencies, acoustic stimulation for low frequencies, and electric stimulation for middle frequencies and/or all frequencies).

Embodiments of the invention may be implemented in whole or in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for auditory prostheses other than cochlear implants such as an auditory brainstem implant—with the electrical stimuli presented by electrodes within or adjacent to the cochlear nucleus—or the auditory midbrain implant—with the electrical stimuli presented by electrodes on or within the inferior colliculus. Furthermore, the acoustic stimuli for some embodiments of the invention could be presented as mechanical vibrations at the round window membrane of the cochlea 104, as opposed to sound waves in the ear canal or external to the body, or as opposed to mechanical vibrations applied to one or more of the three bones in the middle ear 103.

What is claimed is:

1. A method of generating stimulus signals for an auditory prosthesis system, the method comprising:
    processing an acoustic audio signal to represent:
        i. a low frequency signal conveying lower audio frequency information including periodicity and fundamental frequency characteristics, and
        ii. a high frequency signal conveying higher audio frequency information including band-pass envelope characteristics;
    providing the low frequency signal to an associated low frequency stimulator of the auditory system of a patient; and
    providing the high frequency signal to an associated high frequency stimulator of the auditory system of the patient including a cochlear implant electrode array having a plurality of high frequency stimulation electrodes for applying the high frequency signal to nearby neural tissue, wherein the high frequency stimulator provides to each stimulation electrode a sequence of electric stimulation pulses at a pulse rate of less than 100 Hz.

2. A method according to claim 1, wherein the low frequency stimulator includes one or more low frequency electrodes in the electrode array, separate from the high frequency stimulation electrodes, for applying the low frequency signal to nearby neural tissue.

3. A method according to claim 2, wherein the one or more low frequency electrodes are closer to an apical end of the electrode array than the high frequency stimulation electrodes.

4. A method according to claim 1, wherein the cochlear implant electrode array contains more than 12 stimulation electrodes.

5. A method according to claim 1, wherein the cochlear implant electrode array contains at least 16 stimulation electrodes.

6. A method according to claim 1, wherein the low frequency signal includes audio frequency information below about 300 Hz and the high frequency signal includes audio frequency information above about 300 Hz.

7. A method according to claim 1, wherein the low frequency stimulator includes an acoustic-mechanical stimulation module for applying the low frequency signal as an acoustic-mechanical input directed to the middle ear of the patient.

8. A method according to claim 7, wherein the acoustic-mechanical stimulation module includes a conventional hearing aid, a middle ear implant, an electro-mechanical transducer adapted to stimulate the round window membrane of the cochlea, an electro-mechanical transducer adapted to stimulate the round window membrane or the fluid of the cochlea, or vibrational stimulation of cerebral fluid or cerebral structures.

9. A method according to claim 1, wherein the high frequency signal includes an anti-hum jitter component.

10. An auditory prosthesis system comprising:
a sound pre-processor for initial processing of an input acoustic audio signal to form a pre-processed audio signal;
a low frequency processor for receiving the pre-processed audio signal to determine a low frequency signal conveying lower audio frequency information including periodicity and fundamental frequency characteristics;
a high frequency processor for receiving the pre-processed audio signal to determine a high frequency signal conveying higher audio frequency information including band-pass envelope characteristics;
a low frequency stimulator for delivering a low frequency stimulation signal based on the low frequency signal to the auditory system of a patient; and
a high frequency signal stimulator including a cochlear implant electrode array having a plurality of high frequency stimulation electrodes for delivering a high frequency stimulation signal based on the high frequency signal to o nearby neural tissue in the auditory system of the patient, wherein the high frequency stimulator provides to each high frequency stimulation electrode a sequence of electric pulses at a pulse rate of less than 100 Hz.

11. An auditory prosthesis system according to claim 10, wherein the low frequency stimulator includes one or more low frequency electrodes in the electrode array, separate from the high frequency stimulation electrodes, for applying the low frequency stimulation signal to nearby neural tissue.

12. An auditory prosthesis system according to claim 11, wherein the one or more low frequency electrodes are closer to an apical end of the electrode array than the high frequency stimulation electrodes.

13. An auditory prosthesis system according to claim 10, wherein the cochlear implant electrode array contains more than 12 stimulation electrodes.

14. An auditory prosthesis system according to claim 13, wherein the cochlear implant electrode array contains at least 16 stimulation electrodes.

15. An auditory prosthesis system according to claim 10, wherein the low frequency signal includes audio frequency information below about 300 Hz and the high frequency signal includes audio frequency information above about 300 Hz.

16. An auditory prosthesis system according to claim 10, wherein the low frequency stimulator includes an acoustic-mechanical stimulation module for applying the low frequency stimulation signal as an acoustic-mechanical input directed to the middle ear of the patient.

17. An auditory prosthesis system according to claim 16, wherein the acoustic-mechanical stimulation module includes a conventional hearing aid, a middle ear implant, an electro-mechanical transducer adapted to stimulate the round window membrane of the cochlea, an electro-mechanical transducer adapted to stimulate the round window membrane or the fluid of the cochlea, or vibrational stimulation of cerebral fluid or cerebral structures.

18. An auditory prosthesis system according to claim 10, wherein the low frequency stimulation signal includes an anti-hum jitter component.

* * * * *